(12) United States Patent
Lee et al.

(10) Patent No.: US 12,376,836 B2
(45) Date of Patent: Aug. 5, 2025

(54) MICROFLUIDIC DEVICE FOR DETECTING BIOMOLECULES IN SWEAT AND WEARABLE BIOSENSOR PATCH USING THE SAME

(71) Applicant: RESEARCH & BUSINESS FOUNDATION SUNGKYUNKWAN UNIVERSITY, Suwon-si (KR)

(72) Inventors: Nae Eung Lee, Suwon-si (KR); Han Byeol Lee, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 930 days.

(21) Appl. No.: 17/161,736

(22) Filed: Jan. 29, 2021

(65) Prior Publication Data

US 2021/0228192 A1    Jul. 29, 2021

(30) Foreign Application Priority Data

Jan. 29, 2020 (KR) ........................ 10-2020-0010235

(51) Int. Cl.
| | | |
|---|---|---|
| A61B 10/00 | (2006.01) | |
| A61B 5/00 | (2006.01) | |
| A61B 5/145 | (2006.01) | |
| A61B 5/1477 | (2006.01) | |
| B01L 3/00 | (2006.01) | |

(52) U.S. Cl.
CPC ...... *A61B 10/0064* (2013.01); *A61B 5/14517* (2013.01); *A61B 5/6833* (2013.01); *B01L 3/502707* (2013.01); *B01L 3/502715* (2013.01); *B01L 3/502738* (2013.01); *A61B 5/1477* (2013.01); *A61B 2562/12* (2013.01); *B01L 2200/027* (2013.01); *B01L 2200/12* (2013.01); *B01L 2200/16* (2013.01); *B01L 2300/0636* (2013.01); *B01L 2300/161* (2013.01);

(Continued)

(58) Field of Classification Search
CPC ............ A61B 10/0064; A61B 5/14517; A61B 5/6833; A61B 5/1477; A61B 2562/12; B01L 3/502707; B01L 3/502715; B01L 3/502738; B01L 2200/12; B01L 2200/16; B01L 2300/161; B01L 2400/04; B01L 2400/06; B01L 2400/063
See application file for complete search history.

(56) References Cited

U.S. PATENT DOCUMENTS 4,731,075 A * 3/1988 Gallo Mezo .......... A61F 2/2403
                                                    623/2.17
9,057,721 B1 * 6/2015 Marion, Jr. ........... B01L 3/5029

(Continued)

FOREIGN PATENT DOCUMENTS

| KR | 1999-0072013 A | 9/1999 |
| KR | 10-2006-0123103 A | 12/2006 |
| KR | 10-2017-0077975 A | 7/2017 |

*Primary Examiner* — Alex M Valvis
*Assistant Examiner* — Jonathan M Haney
(74) *Attorney, Agent, or Firm* — NSIP Law

(57) ABSTRACT

A microfluidic device for detecting biomolecules in sweat, and a biosensor patch for detecting biomolecules in sweat, in which the microfluidic device and a biosensor are combined, the device and the patch being capable of detecting various target molecules present in sweat by electrochemical signals and also detecting the concentration of a target molecule.

11 Claims, 15 Drawing Sheets

(52) U.S. Cl.
CPC .............. *B01L 2400/0406* (2013.01); *B01L 2400/0605* (2013.01); *B01L 2400/0638* (2013.01)

(56) References Cited

U.S. PATENT DOCUMENTS

| | | | |
|---|---|---|---|
| 11,406,321 B2* | 8/2022 | Model | A61B 5/746 |
| 2006/0057245 A1* | 3/2006 | Haupt | B01L 3/502707 |
| | | | 425/589 |
| 2012/0040468 A1* | 2/2012 | Khaled | B01L 3/502715 |
| | | | 436/95 |
| 2012/0058496 A1* | 3/2012 | Katsuhara | A61B 10/0064 |
| | | | 435/7.92 |
| 2018/0338713 A1* | 11/2018 | Polsky | A61B 5/157 |
| 2019/0069818 A1* | 3/2019 | Prasad | A61B 5/1477 |
| 2020/0315503 A1* | 10/2020 | Heikenfeld | A61B 5/14539 |
| 2021/0145352 A1* | 5/2021 | Rogers | A61B 5/150022 |
| 2022/0211304 A1* | 7/2022 | Dellimore | A61B 5/6833 |

* cited by examiner

MICROFLUIDIC DEVICE FOR DETECTING BIOMOLECULES IN SWEAT AND WEARABLE BIOSENSOR PATCH USING THE SAME

CROSS-REFERENCE TO RELATED APPLICATIONS

This application claims the benefit under 35 USC § 119 (a) of Korean Patent Application No. 10-2020-0010235 filed on Jan. 29, 2020, in the Korean Intellectual Property Office, the entire disclosure of which is incorporated herein by reference for all purposes.

BACKGROUND

Field

The following description relates to a microfluidic device for detecting biomolecules in sweat, a biosensor patch including the same, a method of manufacturing the microfluidic device, and a method of detecting biomolecules in sweat by using the microfluidic device.

Description of Related Art

As interest in personal health increases, personal testing is becoming more common, and such personal diagnostic devices can play an important role in the detection of biomolecules using sweat or interstitial fluid. However, due to the difficulty in sampling for the detection of actual proteins, small molecules, or the like and detecting measurement reactions, the use of these devices is currently limited to enzyme sensor technology for glucose measurement. Therefore, to address these problems, there is a gradually increasing need for a wearable device that is capable of sampling and detecting measurement reactions.

As a wearable device, for sweat sampling, technology for transferring sweat to a measurement device using cotton fabrics, fiber tissues, absorption pads, or the like is common, and research on sweat sampling using a microfluidic device is been conducted. However, this technology is limited to transferring sweat samples to a measurement device, and wearable devices using the same are also limited to detecting ions (sodium and potassium) and biomolecules (glucose and lactic acid) using a color conversion sensor or an electrochemical sensor. For detecting proteins, small molecules, or the like in sweat, to use an affinity-based biosensor in the form of skin attachment, a technology that enables the detection of measurement reactions as well as sweat sampling is required. In the affinity-based biosensor, element technologies such as labeling, washing, and reagent solution injection may be needed, and there is a need to develop a technology for a skin-attachment-type system equipped with all these functionalities.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a microfluidic device provided above a biosensor, the microfluidic device including a fluidic passing layer including an inlet part configured to collect sweat secreted from the skin, a sensing element in communication with the inlet part via a first microchannel and being configured to receive sweat from the inlet part, a reagent storage part in communication with the sensing element part via a second microchannel and being configured to supply a detection reagent to the sensing element part, and a disposer in communication with the sensing element part via a third microchannel and being configured to accommodate sweat of the sensing element part, and a fluidic connection layer including a microfluidic tube arranged in a vertical direction to supply sweat secreted from the skin to the inlet part, a sensing space provided between the sensing element and the biosensor to transfer sweat of the sensing element to the biosensor, and a reagent storage space positioned below the reagent storage part to store the detection reagent, wherein the fluidic connection layer is disposed below the fluidic passing layer.

The first microchannel may include an arch-type flap valve configured to prevent fluid from flowing towards the inlet part.

The second microchannel may include a check valve.

The third microchannel may include a burst valve.

The reagent storage part may include a button having a tapered shape.

The sensing element may include a microchannel configured to induce a capillary phenomenon.

The fluidic passing layer or the fluidic connection layer may have a thickness of 500 μm or less.

The microfluidic device may include a hydrophilic polymer formed on an elastic polymer.

The elastic polymer may include polydimethylsiloxane (PDMS) or polyurethane (PU), and the hydrophilic polymer comprises polyvinylpyrrolidone (PVP), polyethylene glycol (PEG), or (3-mercaptopropyl) trimethoxysilane (MPTMS).

The hydrophilic polymer may be formed in any one or any combination of the inlet part of the fluidic passing layer, the microfluidic tube of the fluidic connection layer, the sensing element of the fluidic passing layer, and the sensing space of the fluidic connection layer.

In another general aspect, there is provided a skin-attachment-type biosensor patch to detect a biomolecule in sweat, the biosensor patch including a fluidic passing layer including an inlet part configured to collect sweat secreted from the skin, a sensing element in communication with the inlet part via a first microchannel and being configured to receive sweat from the inlet part, a reagent storage part in communication with the sensing element part via a second microchannel and being configured to supply a detection reagent to the sensing element part, and a disposer in communication with the sensing element part via a third microchannel and being configured to accommodate sweat of the sensing element part, and a fluidic connection layer including a microfluidic tube arranged in a vertical direction to supply sweat secreted from the skin to the inlet part, a sensing space provided between the sensing element and a biosensor to transfer sweat of the sensing element to the biosensor, and a reagent storage space positioned below the reagent storage part to store the detection reagent, wherein the fluidic connection layer is disposed below the fluidic passing layer, and the biosensor is provided below the fluidic connection layer and comprises a probe configured to detect the biomolecule.

The biosensor may be an affinity-based nanostructure in which a probe may be fixed to a sensor.

The biosensor patch may be stretchable.

In another general aspect, there is provided a method of manufacturing a microfluidic device, the method including fabricating a three-dimensional mold for manufacturing a microfluidic device using a 3D printer, forming a fluidic passing layer and a fluidic connection layer by pouring an elastic polymer solution into the mold and thermally curing the solution, treating the fluidic passing layer and the fluidic connection layer with a hydrophilic polymer, and combining the fluidic passing layer and the fluidic connection layer, subsequent to the treating with the hydrophilic polymer.

Other features and aspects will be apparent from the following detailed description, the drawings, and the claims.

BRIEF DESCRIPTION OF DRAWINGS

FIG. 13 is an example of a graph showing the results of measuring impedance to detect cortisol present in artificial sweat using a biosensor patch is a diagram illustrating an example of.

Figure 1:
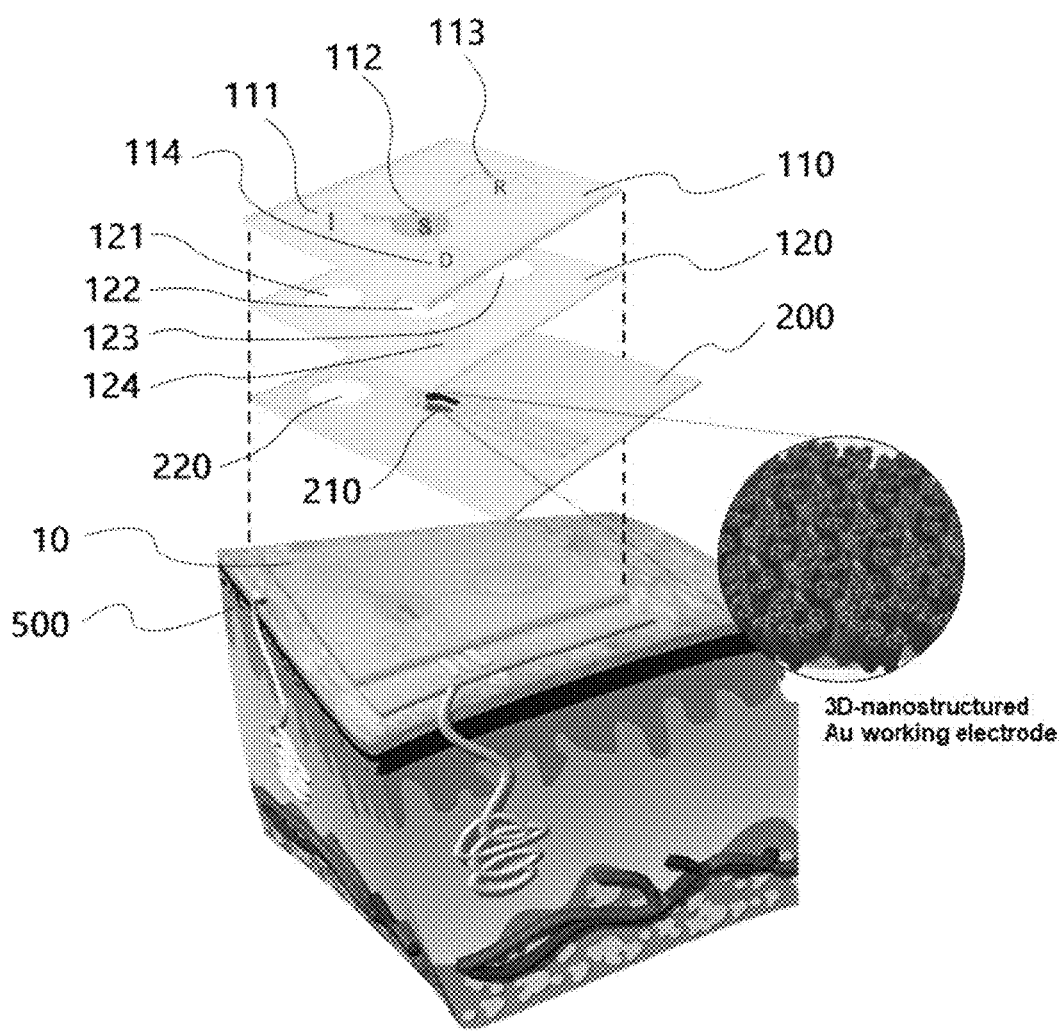
FIG. 1 is a diagram illustrating an example of a stretchable biosensor patch that is attachable to the skin and to which a microfluidic device is coupled.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Hereinafter, examples will be described in detail with reference to the accompanying drawings. The scope of the examples is not limited to the descriptions provided in the present specification. The examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Figure 2:
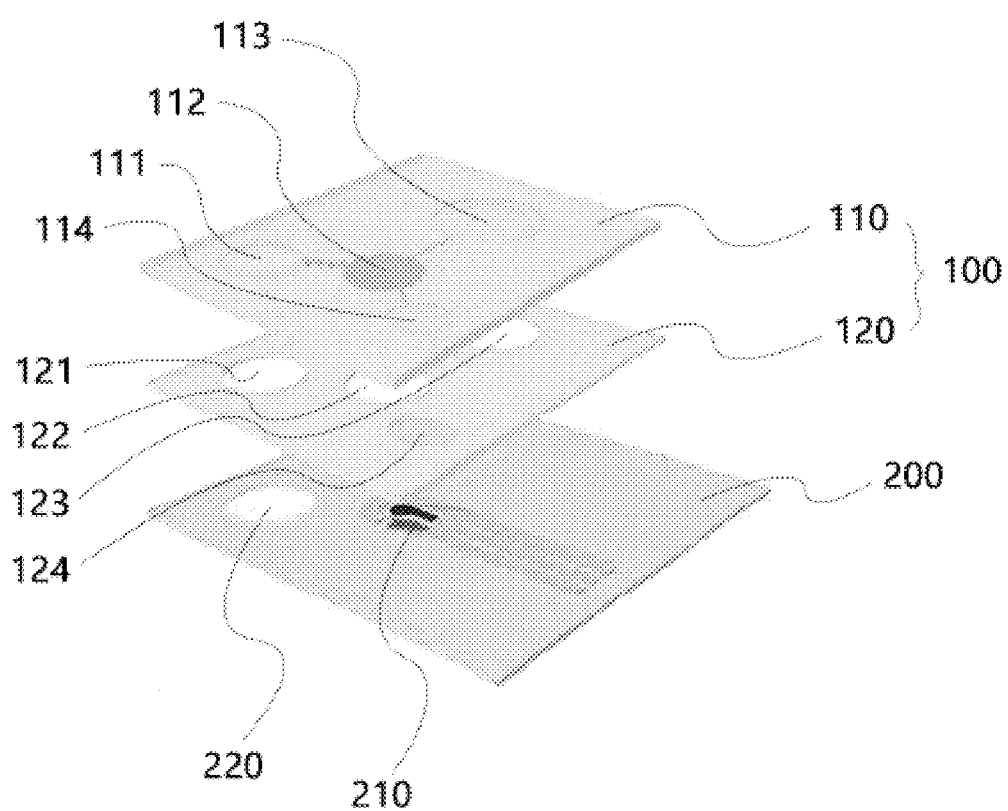
FIG. 2 is a diagram illustrating an example of a coupling relationship among a fluidic passing layer, a fluidic connection layer, and a biosensor in a biosensor patch.

FIG. 1 is a diagram illustrating an example of a biosensor patch 10 disposed on a skin 500 of a subject, and FIG. 2 is a diagram illustrating an example of the biosensor patch 10 illustrated in FIG. 1.

Referring to FIGS. 1 and 2, the biosensor patch 10 may include a microfluidic device 100 having a double layer and a biosensor 200.

In an example, the microfluidic device 100 is arranged above the biosensor 200 and includes a fluidic passing layer ("FPL") 110 and a fluidic connection layer ("FCL") 120. In FIGS. 1 and 2, I is the inlet unit, S is the sensing element unit, R is the reagent storage unit, and D is the disposal unit.

The fluidic passing layer 110 is disposed above the fluidic connection layer 120, and includes an inlet part 111 through which sweat secreted from the skin is collected, a sensing element part 112 that is in communication with the inlet part 111 via a microchannel to receive sweat from the inlet part 111, a reagent storage part 113 that is in communication with the sensing element part 112 via a microchannel to supply a detection reagent to the sensing element part 112, and a disposal part 114 that is in communication with the sensing element part 112 via a microchannel to accommodate sweat of the sensing element part 112.

The fluidic connection layer 120 is disposed below the fluidic passing layer 110 and above the biosensor 200. In an example, the fluidic connection layer 120 includes: a microfluidic tube 121 arranged in a vertical direction to supply sweat secreted from the skin, a sensing space 122 that is provided between the sensing element part 112 and the biosensor 200 to transfer sweat of the sensing element part 112 to the biosensor 200, and a reagent storage space 123 that is positioned below the reagent storage part 113 to store a reagent.

The inlet part 111 of the fluidic passing layer 110 and the microfluidic tube 121 of the fluidic connection layer 120 may be in communication with each other to form one space when the layers are attached to each other to constitute the microfluidic device 100. In addition, when the biosensor 200 is attached to the microfluidic device 100 to constitute the biosensor patch 10, the inlet part 111, the microfluidic tube 121, and an inlet 220 of the biosensor may be in communication with one another to form one space, and sweat may be introduced into and stored in the space. For convenience of description, the inlet part 111, the microfluidic tube 121, and the inlet 220 are given different names and reference numerals, but when the layers are attached to constitute the biosensor patch 10, these parts may function as an inlet unit I, which is a single space. In an example, the shape of the inlet part 111, the microfluidic tube 121, or the inlet 220 may be a circular shape. Other shapes of the inlet unit I, such as, for example, a polygonal shape such as a triangular, tetragonal, pentagonal, or hexagonal shape may be appropriately used without departing from the spirit and scope of the illustrative examples described. In the biosensor patch 10, the inlet unit I (see FIG. 3) formed as a single space may have a volume of 5 µL to 50 µL, such as, for example, 7 µL to 20 µL and 32 µL to 50 µL.

The sensing element part 112 of the fluidic passing layer 110 and the sensing space 122 of the fluidic connection layer 120 may be in communication with each other to form one space when the layers are attached to constitute the microfluidic device 100, and a probe 210 attached to the biosensor 200 may be provided below the space. For convenience of description, the sensing element part 112 and the sensing space 122 are given different names and reference numerals, but when the layers are attached to constitute the microfluidic device 100, may function as a sensing element unit S, which is a single space. The shape of the sensing element part 112 or the sensing space 122 may be a circular shape. Other shapes of the sensing element unit S, such as, for example, a polygonal shape such as a triangular, tetragonal, pentagonal, or hexagonal shape may be appropriately used without departing from the spirit and scope of the illustrative examples described. In the biosensor patch 10, the sensing element unit S (see FIG. 3) formed as a single space may have a volume of 20 µL to 50 µL, such as, for example, 33 µL to 37 µL and 34 µL to 36 µL.

The reagent storage part 113 of the fluidic passing layer 110 and the reagent storage space 123 of the fluidic connection layer 120 may be in communication with each other to form one space when the layers are attached to constitute the microfluidic device 100, and a detection reagent may be pre-stored in the space in a process of manufacturing the biosensor patch 10. For convenience of description, the reagent storage part 113 and the reagent storage space 123 are given different names and reference numerals, but when the layers are attached to constitute the microfluidic device 100, may function as a reagent storage unit R (see FIG. 3), which is a single space. The shape of the reagent storage part 113 or the reagent storage space 123 may be a circular shape. Other shapes of the reagent storage unit R, such as, for example, a polygonal shape such as a triangular, tetragonal, pentagonal, or hexagonal shape may be appropriately used without departing from the spirit and scope of the illustrative examples described. In the biosensor patch 10, the reagent storage unit R (see FIG. 3) formed as a single space may have a volume of 30 µL to 100 µL, such as, for example, 75 µL to 85 µL and 78 µL to 82 µL.

The disposal part 114 may be provided only in the fluidic passing layer 110. In other specific embodiments, the disposal part 114 of the fluidic passing layer 110 and a disposal space 124 of the fluidic connection layer 120 may be attached to each other to form the microfluidic device 100, and in this case, may be in communication with each other to form one space. The space allows fluid, e.g., sweat, remaining in the sensing element unit S (see FIG. 3) to be transferred so that the detection reagent can be introduced into the sensing element unit S. For convenience of description, the disposal part 114 and the disposal space 124 are given different names and reference numerals, but when the layers are attached to constitute the microfluidic device, may function as a disposal unit D (see FIG. 3), which is a single space. The shape of the disposal part 114 or the disposal space 124 may be a circular shape. Other shapes of the disposal unit D, such as, for example, a polygonal shape such as a triangular, tetragonal, pentagonal, or hexagonal shape may be appropriately used without departing from the spirit and scope of the illustrative examples described.

The inlet part 111, the reagent storage part 113, and the disposal part 114 of the fluidic passing layer 110, or the microfluidic tube 121, the reagent storage space 123, and the disposal space 124 (when included) of the fluidic connection layer 120 are each independently connected to the sensing element part 112 of the fluidic passing layer 110 or the sensing space 122 of the fluidic connection layer 120 via microchannels 115 to 117.

Figure 4A:
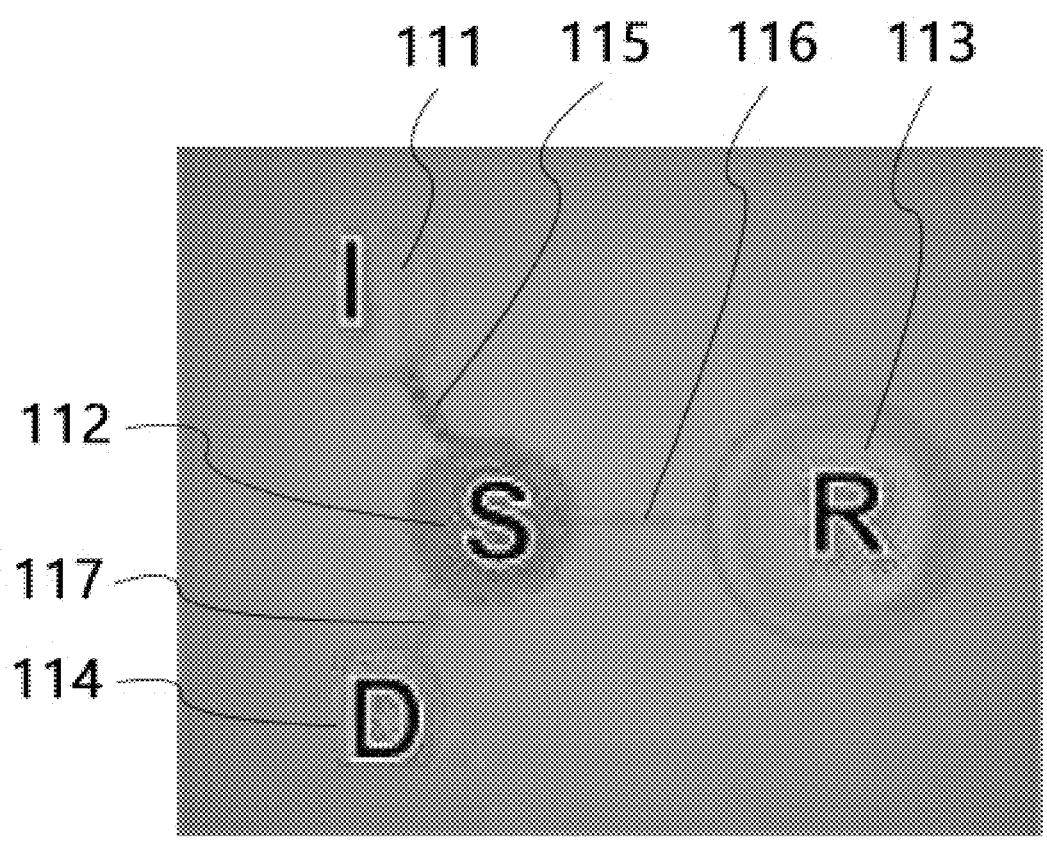
FIG. 4A is a diagram illustrating an example of a fluidic passing layer.
Figure 4B:
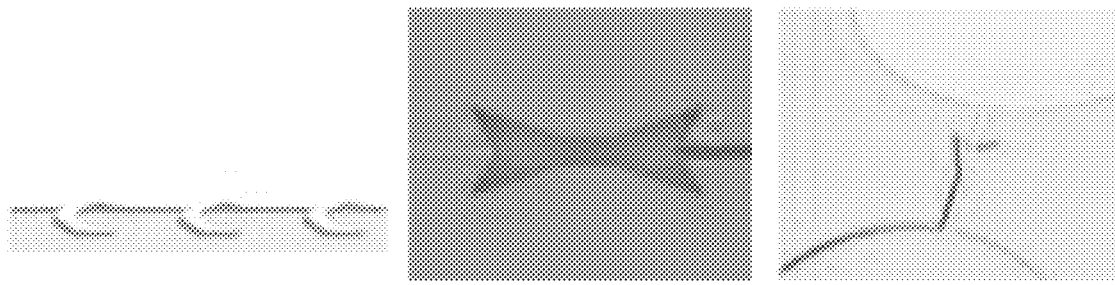
FIG. 4B is a diagram illustrating an example of an arch-type flap valve, a check valve, and a burst valve in the order from the left side.

More specifically, as illustrated in FIG. 4A, the inlet part 111 and/or the microfluidic tube 121 are/is in communication with the sensing element part 112 and/or the sensing space 122 via a first microchannel 115 so that sweat introduced into the inlet part 111 can be transferred to the sensing element part 112 or the sensing space 122. The first microchannel 115 may include a venous valve—mimicking arch-type flap valve (see the left image of FIG. 4B) that allows fluid to flow only towards the sensing element part 112 or the sensing space 122 and prevents fluid from flowing towards the inlet part 111 or the microfluidic tube 121.

The reagent storage part 113 and/or the reagent storage space 123 are/is in communication with the sensing element part 112 and/or the sensing space 122 via a second microchannel 116 so that the detection reagent stored in the reagent storage part 113 or the storage space 123 can be transferred to the sensing element part 112 or the sensing space 122. The second microchannel 116 may include a check valve (see the middle image of FIG. 4B) that does not allow the detection reagent to flow bidirectionally at a certain pressure or less.

Figure 5:
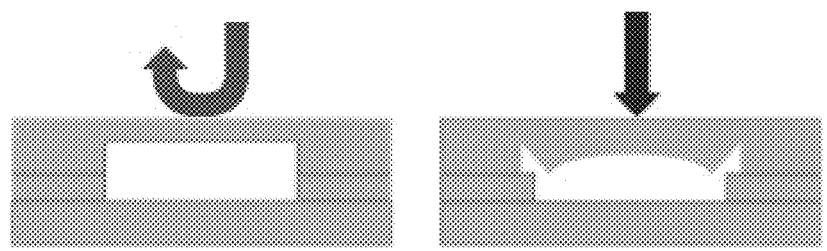
FIG. 5 is a diagram illustrating an example of comparing a reagent storage unit button having a tapered shape (right side) with a button having a general shape (left side).

In an example, the reagent storage part 113 may be a button having a tapered shape. The button having a tapered shape is a device for transferring the detection reagent to the sensing element part 112 or the sensing space 122 by applying a pressure at a desired time point, and as illustrated in FIG. 5, may include a protrusion and a groove, unlike buttons having a general shape, and accordingly, when the button is pushed once, the protrusion and the groove are fastened, thus preventing the button from returning to its original state. Thus, it is possible to prevent the backflow of a reagent into the reagent storage part 113 or the reagent storage space 123, caused by a negative pressure generated by the button returning to its original state.

The sensing element part 112 and/or the sensing space 122 are/is in communication with the disposal part 114 and/or the disposal space 124 via a third microchannel 117 so that sweat present in the sensing element part 112 or the sensing space 122 can be transferred to the disposal part 114 or the disposal space 124. The third microchannel 117 may include a burst valve (see the right image of FIG. 4B) that allows the remaining fluid to flow when a certain pressure or higher is applied.

Figure 7:
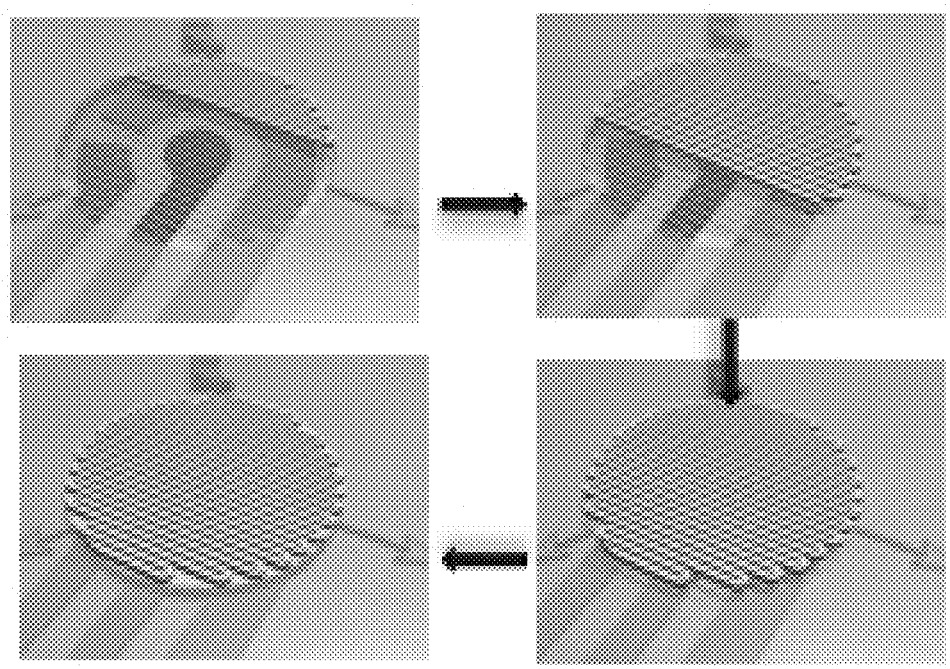
FIG. 7 is a diagram illustrating an example of a microchannel with a zigzag pattern, formed in a sensing element part.

In an example, the sensing element part 112 may include, therein, a microchannel with a zigzag pattern that facilitates the flow of collected sweat and allows the collected sweat to uniformly spread over the entire area of the sensing element part (see FIG. 7).

Each of the layers constituting the microfluidic device 100 may be formed to a thickness of 500 μm or less through a mold fabricated using a 3D printer.

In an example, the microfluidic device 100 may have a hydrophilic polymer for imparting hydrophilicity formed on an elastic polymer for imparting elasticity, and thus is capable of efficiently absorbing and transferring sweat. The elastic polymer may be, for example, polydimethylsiloxane (PDMS), polyurethane (PU), or the like, and the hydrophilic polymer may be, for example, polyvinylpyrrolidone (PVP), polyethylene glycol (PEG), (3-mercaptopropyl) trimethoxysilane (MPTMS), or the like. In particular, the inlet part of the fluidic passing layer and the microfluidic tube of the fluidic connection layer, the sensing element part of the fluidic passing layer and the sensing space of the fluidic connection layer, or all of them may be treated with the hydrophilic polymer so that sweat secreted from the skin of a subject can be satisfactorily introduced into the microfluidic device.

In an example, the microfluidic device 100 may be coupled to the biosensor 200 including the probe 210 for detecting a biomolecule, thereby constituting the skin-attachment-type biosensor patch 10 for detecting a biomolecule in sweat.

In an example of the biosensor patch 10, the biosensor 200 may include an affinity-based three-dimensional nanostructure in which the probe 210 capable of detecting a target biomolecule is fixed to a sensor, and through this structure, biomolecules present in sweat, e.g., cortisol, may be measured in units of picomoles (pM).

As used herein, the term "biomolecule" refers to a molecule that constitutes a living organism and is needed for the structure, function, signal transduction, and the like of a living organism.

In an example, the biosensor 200 may further include the inlet 220 through which sweat can be introduced.

In an example, the biosensor patch 10 may be attached to the skin of a subject to be analyzed, and more particularly, may be positioned and attached such that the biosensor 200 is in direction contact with the skin, such as arms, legs, or the torso, of a subject. The subject may include animals, for example, mammals (e.g., humans, apes, monkeys, mice, cows, dogs, and cats) to analyze a biomolecule in sweat naturally secreted from the subject, but the present invention is not limited thereto.

In an example, the biosensor patch 10 is stretchable.

The biosensor patch 10 according to an embodiment of the present invention may be disposable.

Figure 3:
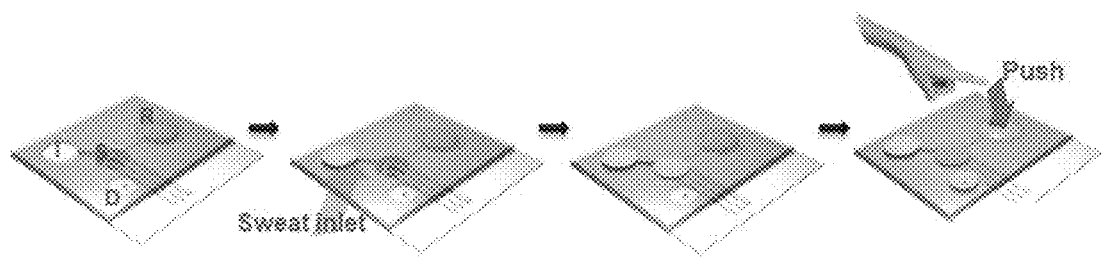
FIG. 3 is a diagram illustrating an example of a process of operating a stretchable biosensor patch using a microfluidic device.

FIG. 3 is a diagram illustrating an example of a process of operating the biosensor patch 10. The process of operating the biosensor patch 10 will be described in detail with reference to FIG. 3.

The biosensor patch 10 is manufactured in the state where a detection reagent is stored in the reagent storage unit R, and sweat is introduced via the inlet unit I and stored. Hydrophilic treatment facilitates the absorption of sweat and the transfer thereof to the sensing element unit S, and enables a certain amount of sweat to be maintained in the sensing element unit S for a latent time for binding with a target biomolecule. After a certain period of time has elapsed, a button of the reagent storage unit R is pressed with a finger, allowing the detection reagent to be transferred to the sensing element unit S and by detecting an electrochemical signal, a target biomolecule is detected. In this case, sweat remaining in the sensing element unit S is transferred to the disposal unit D.

The term "detection reagent" as used herein refers to a reagent containing a redox species required to obtain an electrical signal from a biosensor, or another biomolecule, other chemicals, or the like capable of specifically binding to a biomolecule to be detected, and the detection reagent may be, for example, one or more selected from potassium hexacyanoferrate (III), phosphate-buffered saline (PBS), a potassium chloride (KCl) solution, an antibody, RNA, DNA, a hapten, avidin, streptavidin, neutravidin, protein A, protein G, lectin, selectin, a radioisotope marker, an aptamer, and a substance capable of specifically binding to a tumor marker. However, other detection reagent may be used without deviating from the spirit and scope of the illustrative examples described.

In an example, the detection of a biomolecule using the biosensor patch 10 includes not only determining whether a biomolecule is present or not but also measuring the concentration thereof.

In an example, a method of measuring the concentration of a biomolecule present in sweat of a subject, includes attaching the biosensor patch 10 to a surface of the skin of the subject, allowing sweat absorbed via the inlet unit I to be maintained in the sensing element unit S, pressing a reagent storage unit button to transfer a detection reagent to the sensing element unit S, and detecting an electrochemical signal to detect a target biomolecule. The operations of the method of measuring the concentration of a biomolecule present in sweat of a subject may be performed in the sequence and manner as described, although the order of some operations may be changed or some of the operations omitted without departing from the spirit and scope of the illustrative examples described.

In an example, a method of detecting a biomolecule present in sweat, the method includes attaching the biosensor patch according to the present invention to a surface of the skin, allowing sweat absorbed via an inlet unit to be maintained in a sensing element unit, pressing a reagent storage unit button to transfer a detection reagent to the sensing element unit, and detecting an electrochemical signal to detect a target biomolecule.

Hereinafter, a method of manufacturing the microfluidic device 100 will be described, and the detailed description of the same parts as those of the above-described microfluidic device 100 are incorporated herein by reference. Thus, the above description may not be repeated here.

The method of manufacturing the microfluidic device 100 according to an example includes fabricating a three-dimensional mold for manufacturing the microfluidic device 100, by using a 3D printer, forming the fluidic passing layer 110 and the fluidic connection layer 120 by pouring an elastic polymer solution into the mold and thermally curing the same, treating the fluidic passing layer 110 and the fluidic connection layer 120 obtained in the above process, with a hydrophilic polymer, and combining the fluidic passing layer 110 and the fluidic connection layer 120 that have been subjected to hydrophilic treatment.

In an example, a mold including a pattern of a microfluidic device is fabricated using a 3D printer. The fabrication of a microfluidic device pattern using existing photolithography may be inconvenient because a plurality of two-dimensional pattern layers may have to be stacked to form a three-dimensional shape after the formation of a two-dimensional shape, which may be addressed by fabricating a mold using a 3D printer. In addition, a microfluidic device manufactured through the mold can completely maintain the pattern, and enables the manufacture of a microfluidic device within a short time. Each of layers of the manufactured microfluidic device is treated with a hydrophilic polymer, thereby facilitating the absorption of sweat. The microfluidic device 100 manufactured using the above-described method and the biosensor 200 are coupled to manufacture the biosensor patch 10.

Hereinafter, some examples of manufacture of biosensor patch with microfluidic device, and its various components are described below. However, these examples are provided only to facilitate the understanding of the disclosure and are not intended to limit the scope of the illustrated examples described.

An example of a manufacture of biosensor patch with microfluidic device coupled thereto is described below.

An example of fabrication of mold using 3D printer is as follows.

Figure 6:
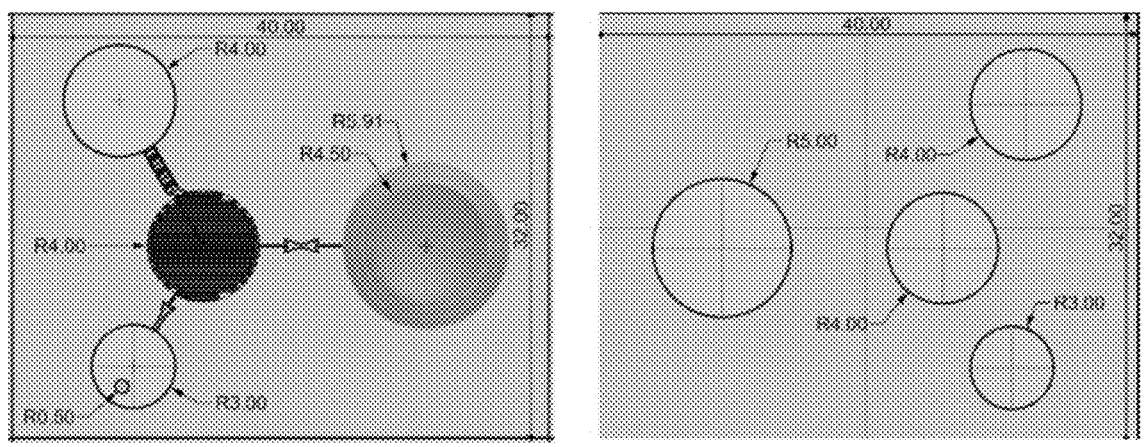
FIG. 6 is a diagram illustrating an example of a mold for manufacturing a microfluidic device (left side, fluidic passing layer; right side, fluidic connection layer).

A mold having a three-dimensional shape is fabricated using a 3D printer as illustrated in FIG. 6 (minimum pattern: 10 μm). The mold is coated with an anti-adhesion material to allow the microfluidic device 100 made of a PDMS material to be easily detached therefrom.

An example of manufacture of Microfluidic Device is as follows. In an example, Plasma or Polymer Treatment for imparting Hydrophilicity is applied.

To perform hydrophilic treatment only on the inlet part 111 and the sensing element part 112 of the fluidic passing layer, oxygen plasma treatment is performed for 30 seconds while the reagent storage part 113 and the disposal part 114 are masked. Oxygen plasma treatment makes a PDMS material hydrophilic for a very short period of time, but the effect does not last for a long time, and thus a long-lasting hydrophilic treatment technique is needed to efficiently collect sweat even after being coupled to the biosensor 200. Thus, a technique for maintaining hydrophilicity for a long time using PVP, which is a hydrophilic polymer, is applied. An appropriate amount of a solution in which PVP is dissolved in ultrapure water to a concentration of 20 wt % is added dropwise to the inlet part 111 and the sensing element part 112, and then the solution is maintained at room temperature for 3 minutes. Thereafter, the resulting structure is washed clean with ultrapure water and stored in an airtight place.

An example of formation of Microchannel in Sensing Element Part is as follows.

When a microchannel is formed, the flow of fluid is facilitated along the microchannel by a capillary phenomenon. As illustrated in FIG. 7, a microchannel having a diameter of 200 μm and a zigzag pattern is formed in the sensing element part 112, so that the entire surface of the sensing element part 112 can be filled with the collected sweat sample.

An example of fabrication of Reagent Storage Unit Button is as follows.

In the case where connection between the reagent storage part 113 and the reagent storage space 123 of the fluidic connection layer 120 is a vertical type (see the left image of FIG. 5), when a button provided above the reagent storage part 113 is pressed with a finger, the button is restored by the elastic force of PDMS, and thus there was a problem in that a reagent was unable to be efficiently transferred to the sensing element part 112 and the sensing space 122. To address the above-described problem, the reagent storage part 113 or a button therefor of the fluidic passing layer 110 is designed to have an angular shape (see the right image of FIG. 5). Accordingly, when the button provided above the reagent storage part 113 is pressed with a finger, the angular shape is engaged with and fixed to the reagent storage space 123 of the fluidic connection layer 120, thus preventing the button from being restored by an elastic force, so that the backflow of a reagent transferred to the sensing element part 112 and the sensing space 122 is prevented.

An example of fabrication of Check Valve and Burst Valve is as follows.

Figure 8:
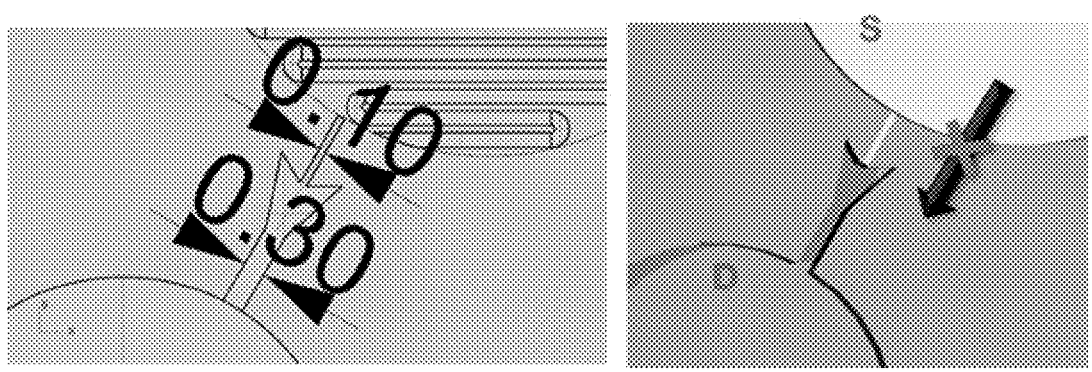
FIG. 8 is a diagram illustrating an example of a design drawing (left side) and a schematic view (right side) of a burst valve provided in a third microchannel that allows a sensing element part to be in communication with a disposal part.
Figure 9:
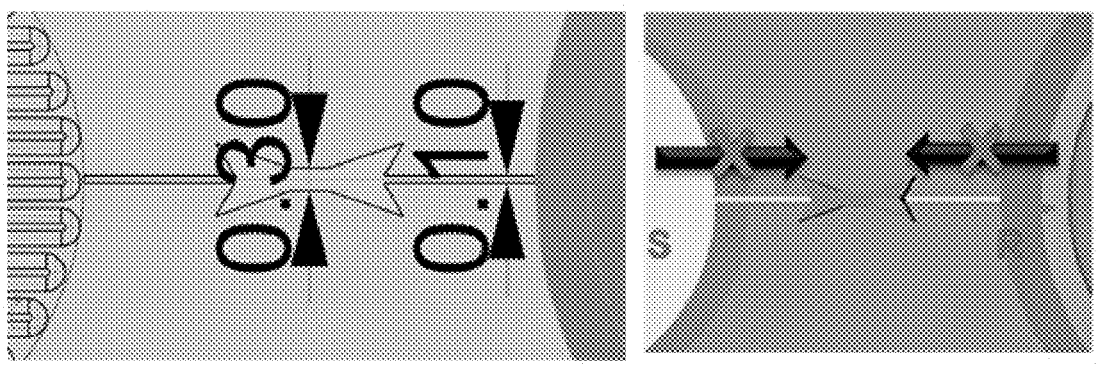
FIG. 9 is a diagram illustrating an example of a design drawing (left side) and a schematic view (right side) of a check valve provided in a second microchannel that allows a sensing element part to be in communication with a reagent storage part.

To confine sweat in the sensing element unit for a certain period of time, a burst valve (FIG. 8) is positioned in the third microchannel 117 that allows the sensing element unit S to be in communication with the disposal unit D, and a check valve (FIG. 9) is positioned in the second microchannel 116 that allows the sensing element unit S to be in communication with the reagent storage unit R. Each microchannel has a width of 100 μm and a height of 200 μm, and the burst valve or the check valve is formed an angle of 120° with respect to the microchannel, thus enabling sweat to be confined in the sensing element unit before a pressure is applied from outside.

An example of fabrication of Flap Valve for preventing Backflow is as follows.

Figure 10:
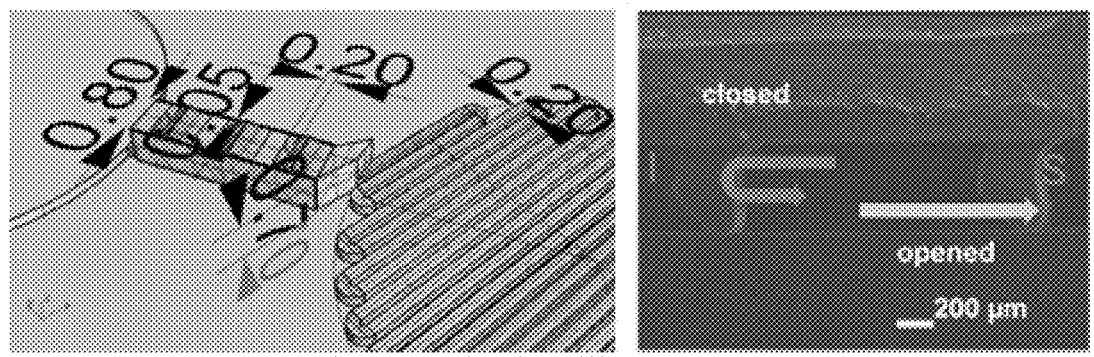
FIG. 10 is a diagram illustrating an example of a design drawing (left side) of a venous valve-mimicking arch-type flap valve provided in a first microchannel that allows a sensing element part to be in communication with an inlet part, and a cross-sectional view (right side) observed using a scanning electron microscope.

To allow sweat to flow only from the inlet unit I towards the sensing element unit S, as illustrated in FIG. 10, a non-return valve (an arch-type flap valve) that mimics a vascular valve structure and prevents backflow is positioned in a first microchannel that allows the inlet unit I to be in communication with the sensing element unit S. A very thin wall (thickness of 50 μm) is formed in a microchannel portion of the mold fabricated using a 3D printer to form a bent valve capable of independently moving in the microchannel. The valve is designed to have a thickness of 200 μm and a height of 700 μm.

An example of manufacture of Biosensor Patch with Microfluidic Device coupled thereto is as follows.

A PDMS solution is poured into the mold fabricated using a 3D printer and thermally cured at 80° C., and then the cured product is detached therefrom to form the fluidic passing layer 110 and the fluidic connection layer 120 to a thickness of 500 μm or less. To combine the two layers, an appropriate amount of a PDMS solution is added dropwise to the fluidic connection layer 120, and then very thinly coated at 2,000 rpm for 30 seconds in a spin coater. Subsequently, the fluidic connection layer 120 is semi-cured on a hot plate at 85° C. for 15 minutes, and then aligned with and coupled to the fluidic passing layer 110, thereby completing the manufacture of a microfluidic device. The microfluidic device is coupled to a biosensor patch using the same method as described above.

An example of Fluid Evaluation under Polyvinylpyrrolidone (PVP) Treatment Conditions is as follows.

After oxygen plasma treatment or PVP treatment for imparting hydrophilicity to PDMS according to the method described above, artificial sweat mixed with a red dye is added dropwise to compare the cross-sections of fluid after 5 hours and 6 days.

Figure 11:
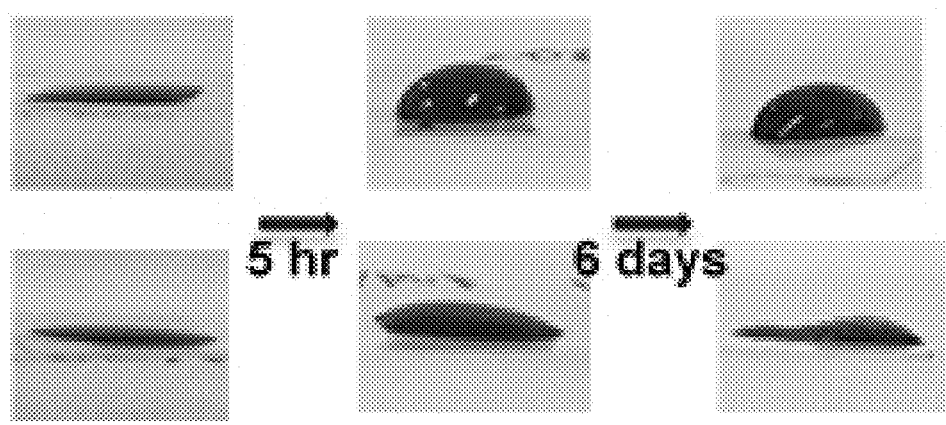
FIG. 11 is a diagram illustrating an example of the cross-sections of fluid 5 hours and 6 days after artificial sweat mixed with a red dye was dropped on PDMS treated with oxygen plasma (top) or PVP (bottom).

As illustrated in FIG. 11, in the case of PDMS subjected to oxygen plasma treatment (top of FIG. 11), the cross-section of fluid exhibits a convex shape after 5 hours, showing a loss of hydrophilicity. In contrast, in the case of PDMS (bottom of FIG. 11) subjected to PVP treatment, the fluid showed a shape of being widely spread on the surface of PDMS even after 6 days, through which it is confirmed that hydrophilicity is maintained for a long period of time.

An example of Fluid Transfer Evaluation according to shape of Reagent Storage Unit Button is as follows.

To prevent the reagent transferred from the reagent storage unit to the sensing element unit from flowing back into the reagent storage unit, in addition to a check valve in a microchannel connecting the two spaces, a button having a tapered shape is used to prevent the formation of a negative pressure generated by the reagent storage unit button being restored by an elastic force and backflow due to this (see the right side of FIG. 5).

Figure 12:
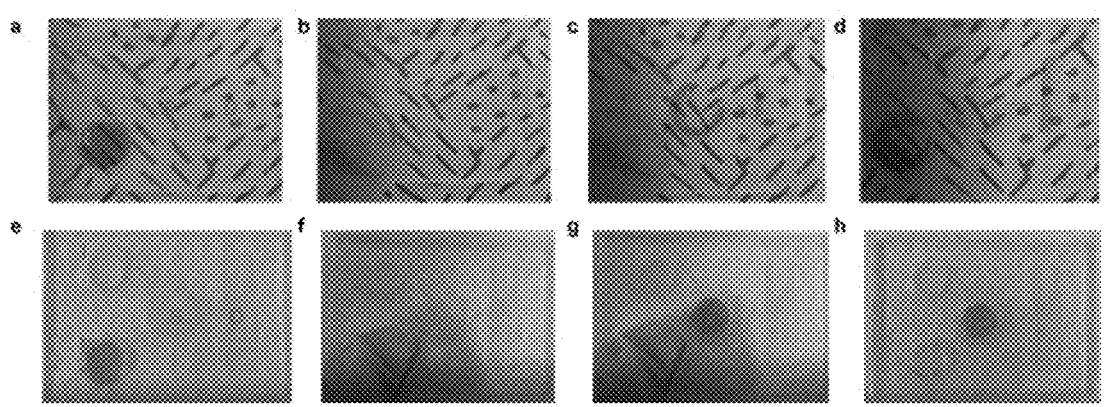
FIG. 12 is a diagram illustrating an example of the results of observing the flow and backflow of fluid in the cases of reagent storage unit buttons having a general shape (top) and a tapered shape (bottom).

As illustrated in FIG. 12, it is confirmed that a button having a general shape returned to its original shape after being pressed by a pressure, and thus the reagent transferred to the sensing element unit flowed back into the reagent storage unit (see top of FIG. 12), whereas, when a button having a tapered shape is used, a reagent can be stably maintained in the sensing element unit without backflow into the reagent storage unit (see bottom of FIG. 12).

An example of Measurement of Concentration of Molecule in Sweat Using Biosensor Patch is as follows.

Figure 13:
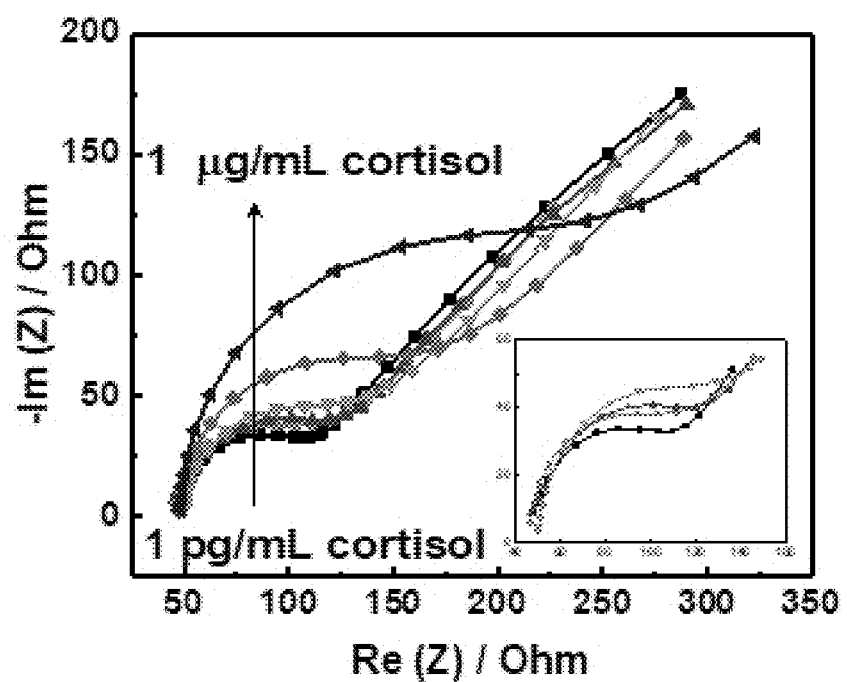

Artificial sweat including cortisol at a concentration of 1 μg/ml to 1 μg/ml is prepared as a target molecule, and then the impedance of the artificial sweat is measured using the biosensor patch 10. As a result, as illustrated in FIG. 13, a graph showing that the greater the concentration of cortisol, the greater the impedance value is obtained.

Figure 14:
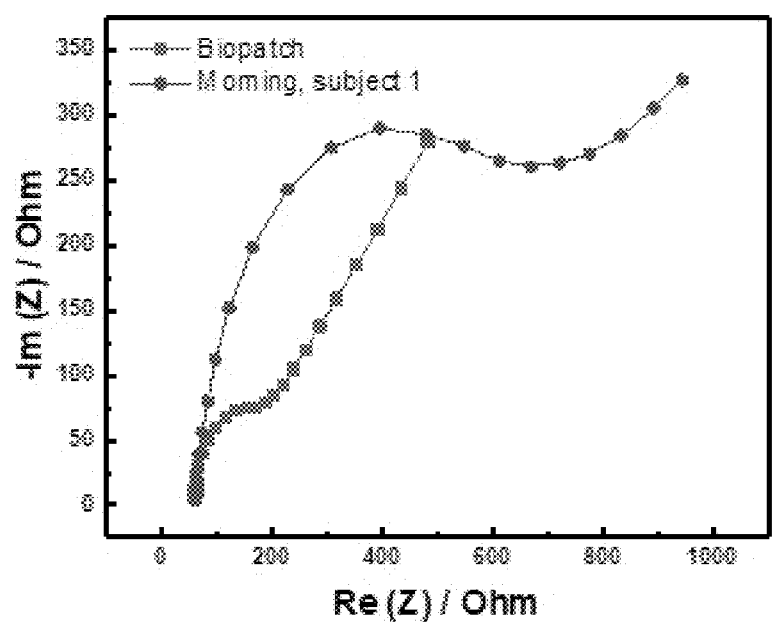
FIG. 14 is an example of a graph showing the results of measuring impedance in samples of sweat generated through exercise after a biosensor patch was attached to a human body.

In addition, the biosensor patch 10 was attached to a human body, and then the impedance of a sweat sample obtained through exercise was measured, and the measurement results thereof are illustrated in FIG. 14.

The embodiments described above disclose a microfluidic device that is attached to an affinity-based biosensor attached to the skin and capable of detecting biomolecules in sweat to transfer sweat for detection and a detection reagent to the biosensor, and a testing apparatus using a biosensor to which the microfluidic device is coupled, thus completing the present invention. The microfluidic device that supplies sweat discharged from the skin to a biosensor.

Also disclosed is a skin-attachment-type biosensor patch for detecting a biomolecule in sweat, a method of manufacturing the microfluidic device, and a method of detecting a biomolecule present in sweat using the biosensor patch.

The embodiments described above relates to a microfluidic device for detecting biomolecules in sweat, and a biosensor patch for detecting biomolecules in sweat, in which the microfluidic device and a biosensor are combined, the device and the patch being capable of detecting various target molecules present in actual sweat by electrochemical signals and also detecting the concentration of a target molecule. Furthermore, the microfluidic device may be coupled to various high-accuracy affinity-based biosensors, which have low detection limitations, and is a system that has various capabilities from sampling to the transfer and measurement of a sample in the state of being attached to a body, and thus can also be applied as a real-time monitoring system. Thus, the microfluidic device is expected to be widely used as a platform that is applicable to a testing apparatus for detecting various biomolecules.

The microfluidic device can be coupled to various high-accuracy affinity-based biosensors, which have low detection limitations, and thus is expected to be used as a platform that is applicable to a testing apparatus for detecting various biomolecules.

While this disclosure includes specific examples, it will be apparent after an understanding of the present disclosure that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A microfluidic device provided above a biosensor, the microfluidic device comprising:
   a fluidic passing layer comprising
      an inlet part configured to collect sweat secreted from skin,
      a sensing element part in communication with the inlet part via a first microchannel and being configured to receive the sweat from the inlet part,
      a reagent storage part in communication with the sensing element part via a second microchannel and comprising a button configured to supply a detection reagent to the sensing element part when pressure is applied to the button, and
      a disposer in communication with the sensing element part via a third microchannel and being configured to accommodate the sweat of the sensing element part; and
   a fluidic connection layer comprising
      a microfluidic tube arranged in a vertical direction to supply sweat secreted from the skin to the inlet part, a sensing space provided between the sensing element part and the biosensor to transfer the sweat of the sensing element part to the biosensor, and a reagent storage space positioned below the reagent storage part to store the detection reagent, wherein the fluidic connection layer is disposed below the fluidic passing layer, and when the button is pushed once, a protrusion and a groove of the button are fastened, preventing the button from returning to its original state.

2. The microfluidic device of claim 1, wherein the first microchannel comprises an arch-type flap valve configured to prevent fluid from flowing towards the inlet part.

3. The microfluidic device of claim 1, wherein the second microchannel comprises a check valve.

4. The microfluidic device of claim 1, wherein the third microchannel comprises a burst valve.

5. The microfluidic device of claim 1, wherein the reagent storage part wherein the button has a tapered shape.

6. The microfluidic device of claim 1, wherein the fluidic passing layer or the fluidic connection layer has a thickness of 500 µm or less.

7. The microfluidic device of claim 1, wherein the microfluidic device comprises a hydrophilic polymer formed on an elastic polymer.

8. The microfluidic device of claim 7, wherein the elastic polymer comprises polydimethylsiloxane (PDMS) or polyurethane (PU), and the hydrophilic polymer comprises polyvinylpyrrolidone (PVP), polyethylene glycol (PEG), or (3-mercaptopropyl) trimethoxysilane (MPTMS).

9. The microfluidic device of claim 7, wherein the hydrophilic polymer is formed in any one or any combination of the inlet part of the fluidic passing layer, the microfluidic tube of the fluidic connection layer, the sensing element part of the fluidic passing layer, and the sensing space of the fluidic connection layer.

10. A skin-attachment-type biosensor patch to detect a biomolecule in sweat, the biosensor patch comprising:

a fluidic passing layer comprising
an inlet part configured to collect the sweat secreted from skin,
a sensing element part in communication with the inlet part via a first microchannel and being configured to receive the sweat from the inlet part,
a reagent storage part in communication with the sensing element part via a second microchannel and comprising a button which is configured to supply a detection reagent to the sensing element part when pressure is applied to the button, and
a disposer in communication with the sensing element part via a third microchannel and being configured to accommodate the sweat of the sensing element part; and a fluidic connection layer comprising
a microfluidic tube arranged in a vertical direction to supply the sweat secreted from the skin to the inlet part,
a sensing space provided between the sensing element part and a biosensor to transfer the sweat of the sensing element part to the biosensor, and
a reagent storage space positioned below the reagent storage part to store the detection reagent,
wherein the fluidic connection layer is disposed below the fluidic passing layer, and the biosensor is provided below the fluidic connection layer and comprises a probe configured to detect the biomolecule, wherein
when the button is pushed once, a protrusion and a groove of the button are fastened, preventing the button from returning to its original state.

11. The biosensor patch of claim 10, wherein the biosensor patch is stretchable.

* * * * *